United States Patent [19]

Katerinopoulos et al.

[11] Patent Number: 5,501,980

[45] Date of Patent: Mar. 26, 1996

[54] BENZAZOLYLCOUMARIN-BASED ION INDICATORS

[75] Inventors: Haralambos E. Katerinopoulos, Crete; Helene Iatridou, Salonica; Evangelia Foukaraki, Crete, all of Greece; Mohammad N. Malekzadeh, Eugene; Michael A. Kuhn, Eugene; Richard P. Haugland, Eugene, all of Oreg.

[73] Assignee: Molecular Probes, Inc., Eugene, Oreg.

[21] Appl. No.: 247,013

[22] Filed: May 20, 1994

[51] Int. Cl.$^6$ ................................. G01N 33/20
[52] U.S. Cl. ................. 436/74; 436/73; 436/79; 436/172; 436/63; 548/159; 548/215; 548/463
[58] Field of Search ................. 436/73, 74, 79, 436/172, 63; 548/159, 215, 463

[56] References Cited

U.S. PATENT DOCUMENTS 4,544,496  10/1985  Claussen et al. ............... 549/288 X (List continued on next page.)

FOREIGN PATENT DOCUMENTS 3738933  5/1989  Germany.

OTHER PUBLICATIONS

G. M. Huitink Proc. Indiana Acad. Sci. 1972, 82, 161–166.
T. G. Papazoglou et al., *Proc. SPIE–Int. Soc. Opt. Eng.* 1993, 1878, 57–64.
R. Y. Tsien *Biochemistry* 1980, 19, 2396.
H. Iatridou et al. *Cell Calcium* 1994, 15, 190–198.
G. C. S. Manku *Aust. J. Chem.* 1971, 24, 925–934
G. M. Huitink *Chem. Abstr.* 1974, 81, 9349a.
G. Grynkiewicz et al. *J. Biol. Chem.* 1985, 260, 3440–3450.
B. Valeur et al., *J. Phys. Chem.* 1992, 96, 6545–6549.
E. U. Akkaya et al. *Anal. Biochem.* 1993, 213, 285–289.
T. G. Papazoglou et al., *Chem. Abstr.* 1993, 119, 198663k.
Haugland, Molecular Probes Handbook of Fluorescent Probes and Research Chemicals Set 20 (1992).
Tsien, Biochemistry, 19, 2396 (1980).
Smith et al., J. Chem. Soc. Perkin Trans., 2, 1195 (1993).
Pethig, et al., Cell Calcium, 10, 491 (1989).
Haugland, Molecular Probes Handbook of Fluorescent Probes and Research Chemicals, 1992, pp. 111–112.
Akkaya et al., Biophys. J. 66, A162 (1994).
Bioprobes 18 (1993).
Wolfbeis et al., Bull. Chem. Soc. Jpn. 58, 731 (1985).

*Primary Examiner*—James C. Housel
*Assistant Examiner*—Arlen Soderquist
*Attorney, Agent, or Firm*—Allegra J. Helfenstein; Anton E. Skaugset

[57] ABSTRACT

The indicator compounds of the present invention are substituted or unsubstituted BAPTA-type chelators that contain a benzazolyl-coumarin substructure, and the pharmaceutically acceptable non-toxic salts and esters thereof. These compounds are useful for the detection and quantification of polycationic metal ions, particularly $Ca^{2+}$.

The compounds of the invention have the core structure

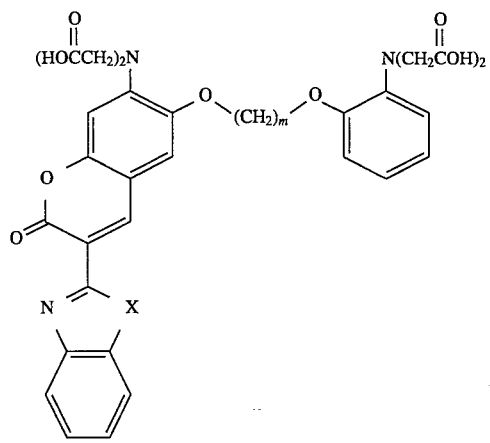

or the structure (Abstract continued on next page.)

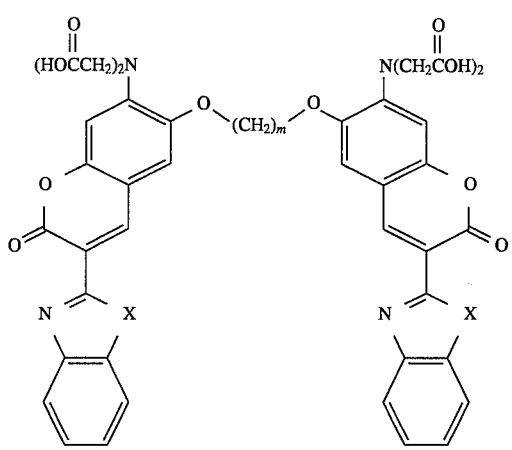

where m=2 or 3 and X can be S, O, or $C(CH_3)_2$.

The above core structures are optionally substituted by substituents that alter the binding affinity of the indicator, shift the spectral properties of the indicator, or act as a reactive site for the preparation of a variety of conjugates.

21 Claims, 10 Drawing Sheets

U.S. PATENT DOCUMENTS

| | | | |
|---|---|---|---|
| 4,603,209 | 7/1986 | Tsien et al. | 548/236 |
| 4,795,712 | 1/1989 | Toner et al. | 436/79 X |
| 4,849,362 | 7/1989 | DeMarinis et al. | 436/79 X |
| 5,049,673 | 9/1991 | Tsien et al. | 546/107 |
| 5,232,858 | 8/1993 | Wolfbeis et al. | 436/79 X |
| 5,310,888 | 5/1994 | Bloczynski et al. | 436/79 X |
| 5,409,835 | 4/1995 | Lakowicz | 436/79 |

+

BENZAZOLYLCOUMARIN-BASED ION INDICATORS

FIELD OF THE INVENTION

This invention relates to fluorescent chelating indicators that selectively bind to polyvalent metal ions in solutions. In particular, the invention relates to fluorescent benzothiazole, benzoxazole or indole derivatives of poly-carboxylate chelators that are used to detect and quantify calcium ions in aqueous solution.

BACKGROUND OF THE INVENTION

Metal ions play an important role in biological systems in regulating enzyme activity, protein structure, and cellular signaling. Metal ions can also have a deleterious effect when present in excess of bodily requirements or capacity to excrete. A large number of natural and synthetic materials are known to selectively or non-selectively bind to or chelate metal ions. Ion chelators are commonly used in solution for in vivo control of ionic concentrations and detoxification of excess metals, and as in vitro buffers. When bound to a fluorophore, ion chelators can often be used as optical indicators of ionic transients.

The detection and quantification of calcium ion ($Ca^{2+}$) levels in biological systems, in particular, has become an important area of investigation in biological and medical research. The most reliable indicators for $Ca^{2+}$ ions to date utilize a tetracarboxylate chelating group based upon the structure of 1,2-bis-2 -aminophenoxyethane-N,N,N',N'-tetraacetic acid (BAPTA), usually in conjunction with a covalently attached fluorophore. Upon binding $Ca^{2+}$ in the BAPTA chelate of the indicator, the fluorescence properties of the attached fluorophore are generally affected in some measurable way (i.e. emission is enhanced or decreased, the wavelength of excitation or emission is altered, etc.). Once the dissociation constant for a specific indicator-$Ca^{2+}$ complex is known, a measurement of the fluorescence properties of a sample containing the indicator allows a determination of in situ $Ca^{2+}$ concentration (Haugland, MOLECULAR PROBES HANDBOOK OF FLUORESCENT PROBES AND RESEARCH CHEMICALS, Set 20 (1992)).

Examples of BAPTA-based fluorescent indicators known in the art include quin-2 (Tsien, BIOCHEMISTRY 19, 2396 (1980)); fura-2, and indo-1 (U.S. Pat. No. 4,603,209 to Tsien et al., 1986); fluo-3 and rhod-2 (U.S. Pat. No. 5,049,673 to Tsien et al. 1991, incorporated by reference); and FURA-RED™ (Molecular Probes, Inc., Eugene, Oreg., trademark for 1-[6-amino-2-(5-oxo-2-thioxo-4 -thiazolidinylidene)methyl-5 -benzofuranyloxy]-2-(2'-amino-5'-methylphenoxy)ethane-N,N,N',N'-tetraacetic acid and the tetraacetoxymethyl ester thereof, U.S. Pat. No. 4,849,362 to DeMarinis, et al. 1989). Additional BAPTA-based fluorescent indicators for $Ca^{2+}$ have been described by Tsien (*Intracellular Measurements of Ion Activities* ANN. REV. BIOPHYS. BIOENG., 12, 91 (1983)), and Smith et al., (J. CHEM. SOC. PERKIN TRANS. 2, 1195 (1993)) however these indicators all have deficiencies in fluorescent response or other properties, thereby limiting their utility.

The indicators fura-2, indo-1 and quin-2 share a common drawback in that the excitation bands for these indicators occur at short wavelengths (340–360 nm). Radiation at these high energy wavelengths has been shown to damage cellular structures, as well as interfere with detection of the resulting fluorescence due to the natural fluorescence many biological materials exhibit at these wavelengths.

The related indicators fluo-3 and rhod-2, containing a fluorescein and rhodamine fluorophore, respectively, were designed to overcome this limitation. These indicators may be used at much longer wavelengths, eliminating the difficulties created by UV irradiation. In addition, these indicators exhibit enhanced fluorescence upon $Ca^{2+}$ binding, simplifying the analysis of $Ca^{2+}$ concentration. The ability to use longer wavelength light both for excitation and emission means that conventional optics and filters can be used in $Ca^{2+}$ determination (in conjunction with flow cytometry or fluorescence microscopy, for example) rather than the specialized and expensive quartz optics required for UV analysis.

It is frequently desirable to have a selection of indicators having a wide range of spectral responses so as to make simultaneous or sequential determination of several analytes, or to be able to demonstrate labeling of spatially resolved sites in biological cells. A novel series of BAPTA-type indicators have been prepared with reactive sites that allow the attachment of a wide range of fluorophores as well as polymolecular assemblies or lipophilic moieties (Copending application REACTIVE DERIVATIVES OF BAPTA USED TO MAKE ION-SELECTIVE CHELATORS, Ser. No. 07/843,360, now U.S. Pat. No. 5,453,517, (filed Feb. 25, 1992) to Kuhn et al., incorporated by reference). By attachment to organelle-targeting peptides, polymeric conjugates of $Ca^{2+}$ indicators have been targeted to cellular organelles, including the nucleus (Copending application BIFUNCTIONAL CHELATING POLYSACCHARIDES, Ser. No. 08/082,269 (filed Jun. 23, 1993) to Kuhn et al., incorporated by reference).

While previous $Ca^{2+}$ indicators, such as those described above, have generally been designed to maximize metal ion affinity, under some circumstances a high binding affinity is undesirable. An ion indicator will have its maximum sensitivity in the range of its dissociation constant for the ion. When the concentration of the ion is more than one log unit above the dissociation constant for the metal, the indicator becomes saturated and unresponsive to further increases in the ion's concentration. For example, a commonly used fluorescent $Ca^{2+}$ indicator, fura-2, with a $Ca^{2+}$ dissociation constant of 224 nM, cannot be used to measure $Ca^{2+}$ levels about 1 μM. In situations where high physiological concentrations of $Ca^{2+}$ are present (as in gap junctions or in some extracellular spaces), indicators with a lower affinity are desirable to ensure a measurable response.

A currently available $Ca^{2+}$ indicator that possesses a lower binding affinity, CALCIUM GREEN™-5N (Molecular Probes, Inc., Eugene, Oreg.) suffers from the drawback that $Ca^{2+}$ binding to the indicator results in an increase in emission intensity only. The indicator displays no wavelength shift in either the excitation or emission spectrum upon binding, which makes the concentration of $Ca^{2+}$ difficult to measure using conventional ratiometric techniques (infra).

The compounds of the present invention, which are based on the benzazolylcoumarin fluorophore, exhibit absorbance and emission that is typically at wavelengths between those of the UV-excited indicators and indicators such as fluo-3, rhod-2, CALCIUM GREEN™ and FURA-RED™. However the compounds of the present invention retain the desirable property of a shift in excitation bands upon binding to metal ions, which allows $Ca^{2+}$ detection or quantification by ratiometric analysis of the excitation spectra of the indicator.

The compounds of the present invention have significant utility as a means of detecting and quantifying metal cation levels in living cells, biological fluids or aqueous solutions. The long wavelength excitation and emission bands of the compounds of the present invention enable their use with a variety of optical devices and require no specialized (quartz) optics, such as are required by indicators which are excited or emit at shorter wavelengths. In addition, the generally weaker affinity of the compounds of the present invention allow the quantification of metal ion levels that are too high for measurement by previously available metal ion indicators that are excited at similar or shorter wavelengths, which simply saturate at higher concentrations. These indicators are suitable for use in fluorescence microscopy, flow cytometry, fluoroscopy, or any other application that currently utilize fluorescent metal ion indicators.

SUMMARY OF THE INVENTION AND DESCRIPTION OF PREFERRED EMBODIMENTS

Figure 1:
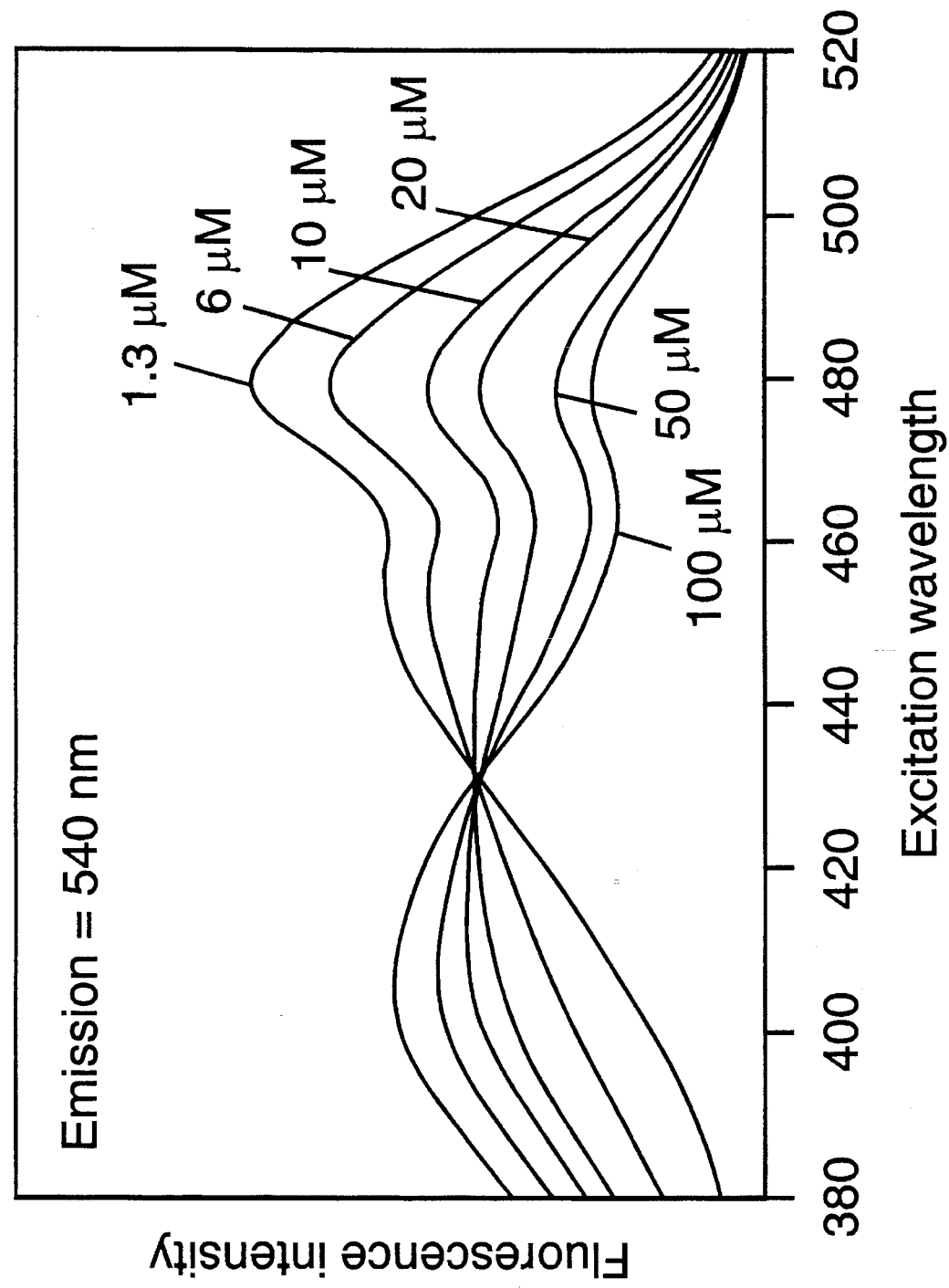
FIG. 1: The effect of increasing $Ca^{2+}$ concentration on the excitation spectrum of Compound 4. Free $Ca^{2+}$ concentrations range from 1.3 to 100 µM as described in Example 21.

The indicator compounds of the present invention are BAPTA-type chelators that contain a benzazolyl-coumarin substructure, and the pharmaceutically acceptable non-toxic salts and esters thereof. The indicators of the present invention are selective for $Ca^{2+}$. The dyes of the present invention possess utility as indicators for $Ca^{2+}$ ions in aqueous solutions, and are selective for $Ca^{2+}$ at physiological concentrations.

Selectivity is defined as preferentially binding to a specific ion within the expected physiological concentration range of that ion. A chelator is considered selective if it has at least a ten-fold discrimination against competing ions. In preferred embodiments, the selectivity of the polycarboxylate chelator is fifty-fold discrimination. More preferably, selectivity of the chelating moiety is greater than 100-fold discrimination against competing ions, at the expected physiological concentration range. In the case of $Ca^{2+}$ detection for biological applications, the ability of an indicator to discriminate between $Ca^{2+}$ and $Mg^{2+}$ (which is present in a concentration of about 1 mM in most cells), is particularly important.

The compounds of the present invention are represented by the following general formula:

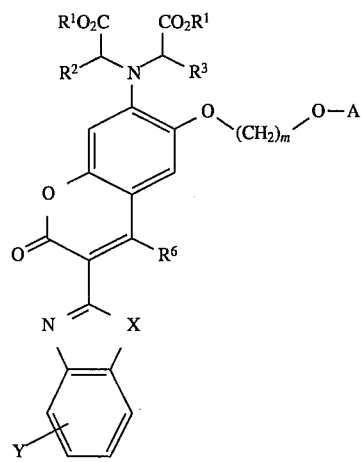

The subscript m is either 2 or 3, giving either an ethylidene or propylidene bridge. Preferably, m is 2.

The chemical moiety A is of the formula

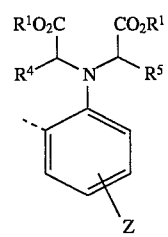

which yields a fluorescent indicator of the formula

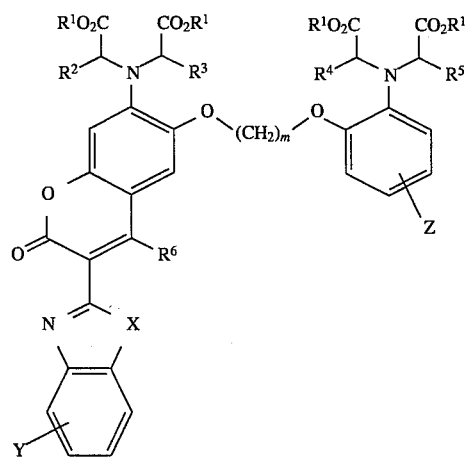

The substituent Z affects the binding affinity and selectivity of the indicator for metal ions as is known in the art (Pethig, et al., CELL CALCIUM 10, 491 (1989)). The substituent Z is H, an alkyl having 1–18 carbons, $—NH_2$, $—NH(C=O)(CH_2)_nCH_3$ (n=0–16), $—CF_3$, F, Cl, Br, I, $—OR^8$, $—CO_2R^9$, or $—OCH_2CO_2R_9$; where $R^8$ is H, an alkyl group having 1–18 carbons, a benzyl ($C_6H_5CH_2—$), an alpha-acyloxyalkyl, an acetate, or a t-butyldimethylsilyl ether; and $R^9$ is H, an alkyl group having 1–17 carbons, a benzyl ($C_6H_5CH_2—$) an alpha-acyloxyalkyl or other pharmaceutically acceptable esterifying group, a t-butyldimethylsilyl ester, or a pharmaceutically acceptable salt. Alternatively, Z is a covalently attached conjugant. Preferably, Z is H, methyl, —$NH_2$ or a covalently attached conjugant. In all embodiments, Z is not nitro.

Alternatively, the extinction coefficient of the coumarin based indicators can be increased by the addition of a second benzazole-coumarin fluorophore. In this case, A is of the formula

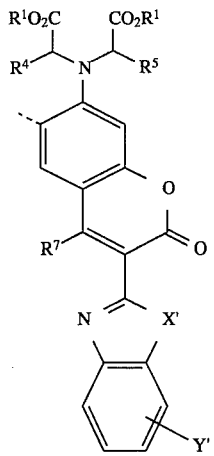

resulting in a fluorescent indicator of the formula

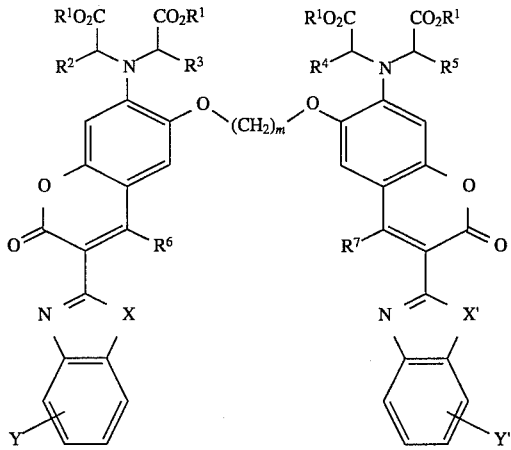

$R^1$ is H, an alkyl group having 1–5 carbons, a benzyl, an alpha-acyloxyalkyl or a pharmaceutically acceptable esterifying group, a t-butyldimethylsilyl ester, or a pharmaceutically acceptable salt. Typically $R^1$ is H, an alkali metal ion or an acetoxymethyl ester.

As used herein, pharmaceutically acceptable salts are non-toxic salts of carboxylic acids known and used in the pharmaceutical industry. Examples include $K^+$, $Na^+$, $Cs^+$, $Li^+$, $Ca^{2+}$, $Mg^{2+}$, $NR_4^+$ salts, where R=H, $C_1$–$C_4$ alkyl, or $C_2$–$C_4$ alkanol or combinations thereof, or combinations of acid salts of these counterions plus free acid groups. Pharmaceutically acceptable esterifying groups are those that form readily hydrolyzable esters which are known and used in the pharmaceutical industry, such as α-acyloxyalkyl esters, especially acetoxymethyl ($CH_3CO_2CH_2$—) esters.

The use of esterification to protect carboxylate groups improves the solubility of the indicator in organic solvents. Appropriate ester groups also allow the indicator to more freely permeate cellular membranes. In particular, chelators that are protected by acetoxymethyl esters penetrate cell membranes, whereupon intracellular esterases cleave the esters hydrolytically, producing the free indicator within the cell.

$R^2$, $R^3$, $R^4$ and $R^5$ are independently H or methyl. Substitution of methyl at one or more of $R^2$, $R^3$, $R^4$ and $R^5$ can be used to modify the affinity, and to a certain extent, the selectivity, of the indicator for specific metal ions (Smith et al., supra). Preferably, $R^2$–$R^5$ are H.

$R^6$ and $R^7$, which may be the same or different, are H, CN, $CH_3$, $CF_3$ or $CONH_2$. Preferably, $R^6$ and $R^7$ are independently H or CN. The substitution of cyano (—CN) or trifluoromethyl ($CF_3$) substituents at the 4-position of related coumarin fluorophores shifts the absorption of those fluorophores to significantly longer wavelengths (for example, U.S. Pat. No. 4,544,496 to Claussen et al.).

X and X', which may be the same or different, are either O, S, or $C(CH_3)_2$, forming a benzoxazole, benzothiazole, or indole heterocycle, respectively. These are collectively referred to herein as benzazoles and, when attached to the coumarin through their 2-positions are collectively referred to as "2-benzazolyl" moieties or substituents. The preferred benzazole heterocycles are benzoxazoles or benzothiazoles.

In all embodiments of the invention, there is extensive delocalization throughout the coumarin substructure and the attached heterocycle. This delocalization enables embodiments of the invention to possess absorbance and fluorescent emission bands that occur at longer wavelengths than those possessed by a BAPTA chelator bound directly to a benzazole fluorophore, or a coumarin fluorophore, only.

Varying the heteroatom of the benzazole ring produces a shift in the spectral and physical properties of the indicator. For example the benzoxazole-coumarin (BOC) BAPTA (Compound 25) has an emission wavelength of 510 nm compared to the benzothiazole-coumarin (BTC) BAPTA (Compound 4), which has an emission of 525 nm. Similarly, while the absorption maximum of BTC BAPTA (Compound 4) shifts from 462 to 401 nm upon forming the $Ca^{2+}$ complex, the absorption maximum of BOC BAPTA (Compound 25) shifts from 447 to 415 upon binding $Ca^{2+}$. Finally, the dissociation constant of the resulting BTC-BAPTA $Ca^{2+}$ complex is 7.0 μM, while the dissociation constant for the related BOC-BAPTA $Ca^{2+}$ complex is 6.6 μM.

Each benzazole substituent is substituted further by Y and Y', respectively, where Y and Y', which may be the same or different, are H, an alkyl having 1–18 carbons, —$NO_2$, —$NH_2$, —NH(C=O)($CH_2)_n$ $CH_3$(n=0–16), —$CF_3$, F, Cl, Br, I, —$OR^8$, —$CO_2R^9$, or —$OCH_2CO_2R^9$; where $R^8$ and $R^9$ are as defined previously. Alternatively Y' is a covalently attached conjugant. Preferably, Y and Y' are independently H, carboxylate, an acetoxymethyl ester of carboxylate or a covalently attached conjugant, more preferably Y and Y' are H. Preferred ring positions for the substituents Y and Y' are the 5- and 6-positions of the benzazole ring systems.

As used herein, a conjugant is a molecule or substance that when attached to the indicator forms an indicator-conjugate. Selected conjugants include, but are not limited to, antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatized nucleic acids (including deoxyribo- and ribonucleic acids), DNA and RNA fragments and derivatized fragments (including single and multi-stranded fragments), natural and synthetic drugs, receptors, virus particles, bacterial particles, virus components, biological cells, cellular components (including cellular membranes and organelles), natural and synthetic lipid vesicles, polymers, polymer particles, polymer membranes, and glass and plastic surfaces and particles.

Preferably the covalently attached conjugant is a polymer film or a polymer microparticle, wherein the polymer is polyacrylamide, or the covalently attached conjugant is a dextran, a modified dextran or glass. Where the conjugant is a polymer microparticle, the particle size is typically greater than 0.01 μm and less than 50 μm. Where the conjugant is a dextran, the dextran typically has a molecular weight greater than 1000 and less than 1,000,000. Attachment of the indicator to a polymeric material can be used to impart ion-sensing properties on that material and to solubilize, insolubilize or otherwise modify the properties of the indicator, the polymer, or both.

The desired indicator-conjugate is most easily prepared when the indicator is initially substituted at Y, Z or Y' by amino ($NH_2$), $-CO_2H$, or $-OCH_2CO_2H$. These substituents can be readily converted to a reactive derivative that is easily attached to polymers, lipids, members of specific binding pairs or other materials. The appropriate reactivities and procedures to prepare the reactive indicators and conjugates is completely described in copending application Ser. No. 07/843,360 (supra).

Synthesis

Useful precursors for preparation of the compounds in this invention have been described in U.S. Pat. Nos. 4,603,209 (supra), 5,049,673 (supra) and 4,849,362 (supra).

Figure 3:
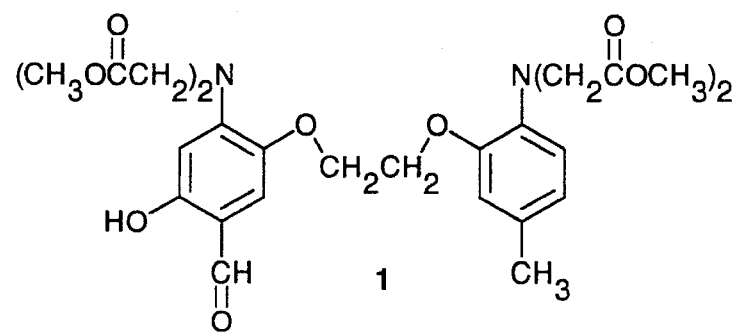
FIG. 3: Synthetic scheme for preparation of Compound 3, as described in Example 1.
Figure 3:
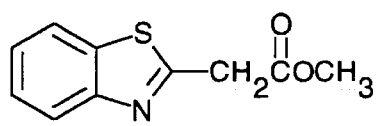
Figure 3:
Figure 3:
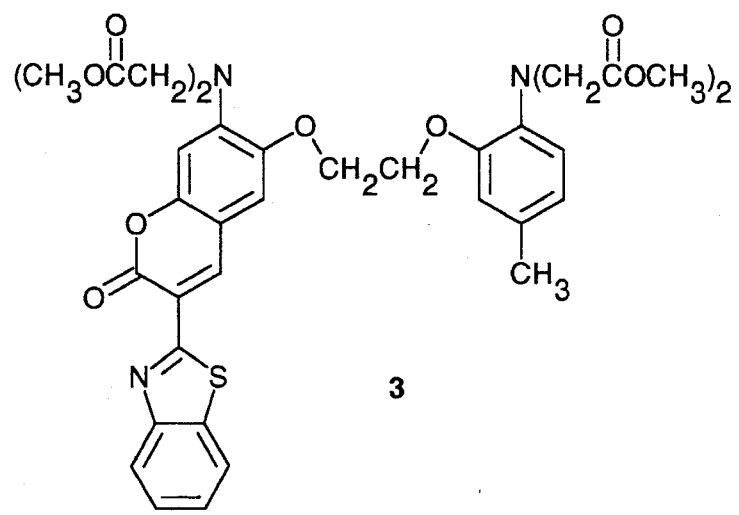
Figure 4:
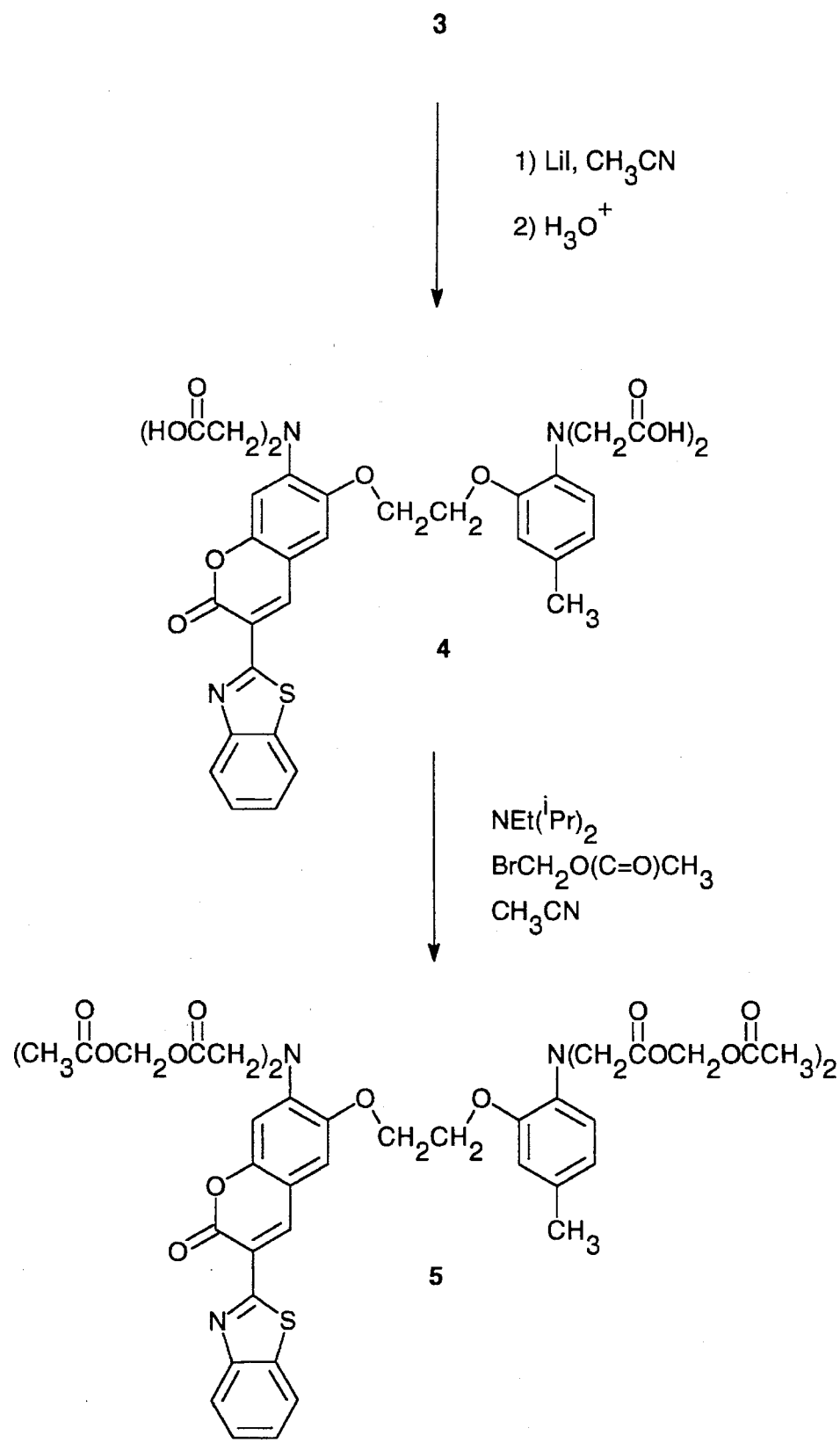
FIG. 4: Synthetic scheme for preparation of Compounds 4 and 5, as described in Examples 2 and 3.

The asymmetric compounds of the present invention are generally prepared from 4-hydroxy-5-formyl-5'-methyl BAPTA tetramethyl ester (Compound 1) previously reported in the synthesis of the indicator fura-2 (U.S. Pat. No. 4,603,209 to Tsien et al., supra). Condensation of I with the methyl ester of benzothiazole (2) gives the fluorescent benzothiazole-coumarin (BTC) BAPTA derivative in high yield (3) (FIG. 3, Example 1). As the coumarin fluorophore is sensitive to strongly basic conditions, the hydrolysis of the methyl esters protecting the tetracarboxylate chelate is effected using LiI in acetonitrile (FIG. 4). The tetralithium salt is water-soluble, and can be precipitated as the free acid (4) or purified by reverse phase chromatography in dilute LiOH, followed by lyophilization.

Figure 5:
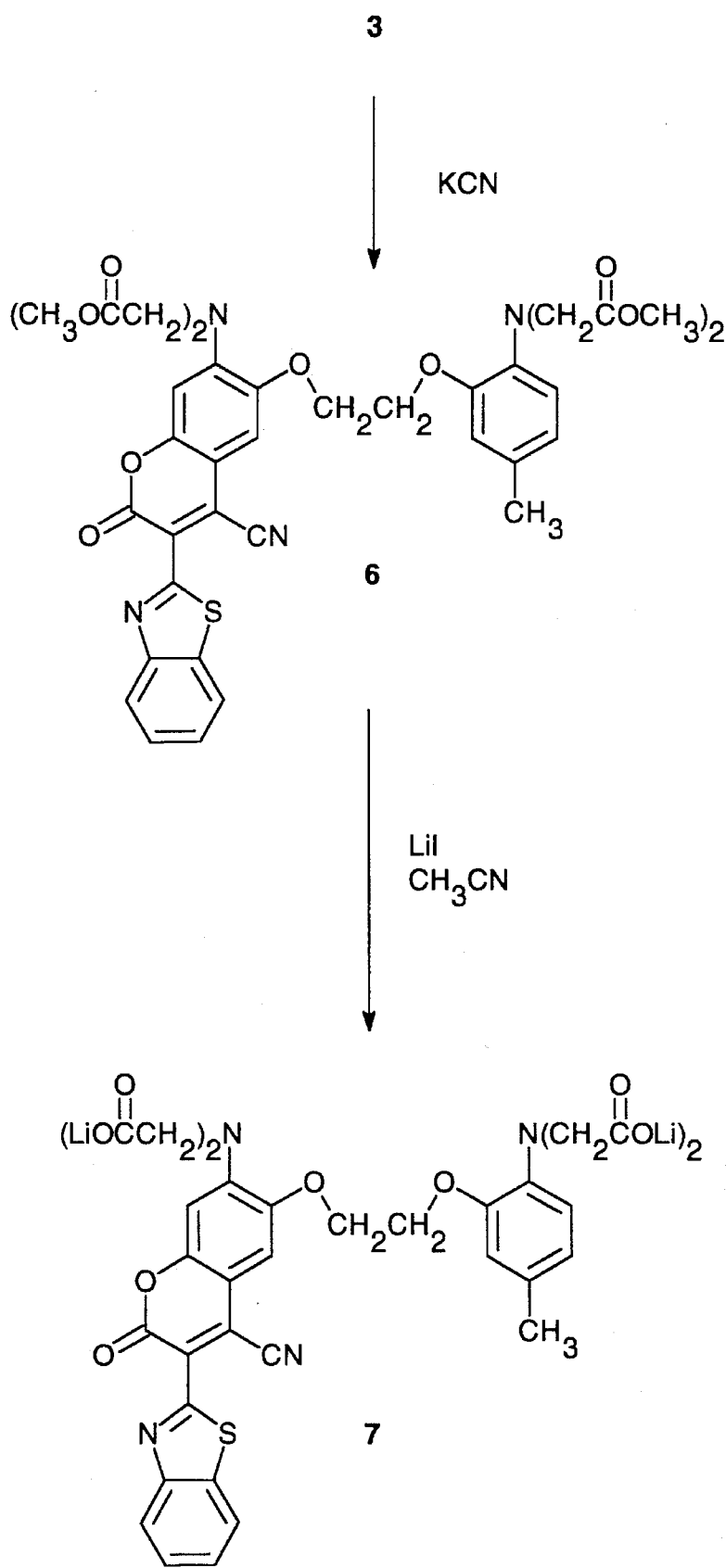
FIG. 5: Synthetic scheme for preparation of Compounds 6 and 7, as described in Examples 4 and 5.
Figure 6:
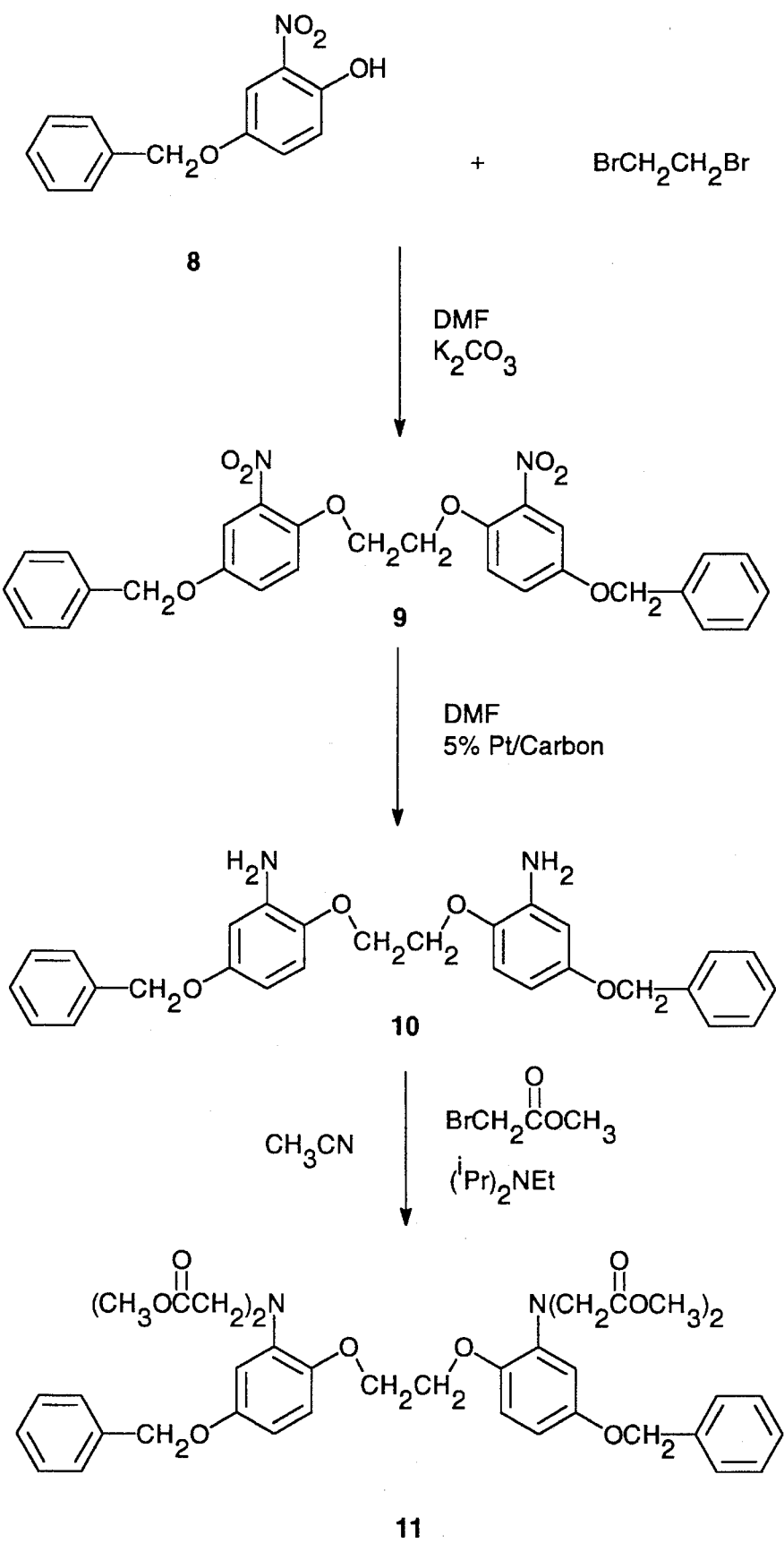
FIG. 6: Synthetic scheme for preparation of Compounds 9, 10 and 11, as described in Examples 6, 7 and 8.

Reaction of the green-fluorescent BTC BAPTA (3) with KCN yields the red-fluorescent cyano-substituted BTC BAPTA, tetramethyl ester (6) (FIG. 5, Example 4). Cleavage of the methyl esters in LiI is similar to that described for BTC BAPTA (Example 5, Compound 7).

Figure 7:
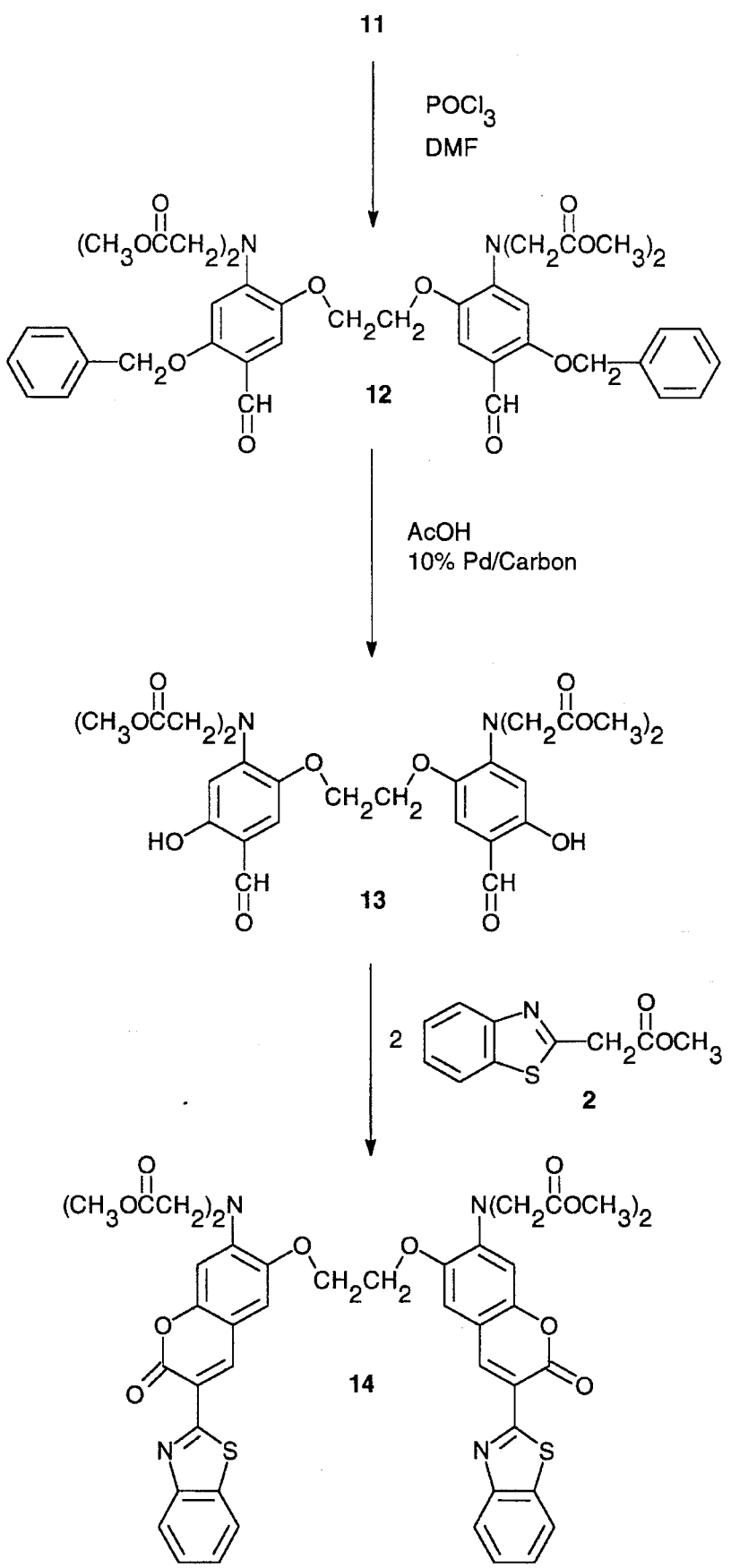
FIG. 7: Synthetic scheme for preparation of Compounds 12, 13 and 14, as described in Examples 9, 10 and 11.

Synthesis of the symmetric bis-BTC BAPTA can be accomplished by condensation of two moles of the α-benzothiazolyl acetate (2) with the symmetric 4,4'-dihydroxy-5,5'-diformyl BAPTA tetramethyl ester (13) (FIG. 7, Example 11). Hydrolysis of the resulting compound (14) gives an indicator (15) with twice the extinction coefficient of BTC BAPTA itself (Example 12). The bis-BTC BAPTA is optionally treated with two equivalents of KCN to give the dicyano indicator, or treated with only one equivalent of KCN to give the asymmetric BTC/cyano-BTC BAPTA.

Figure 8:
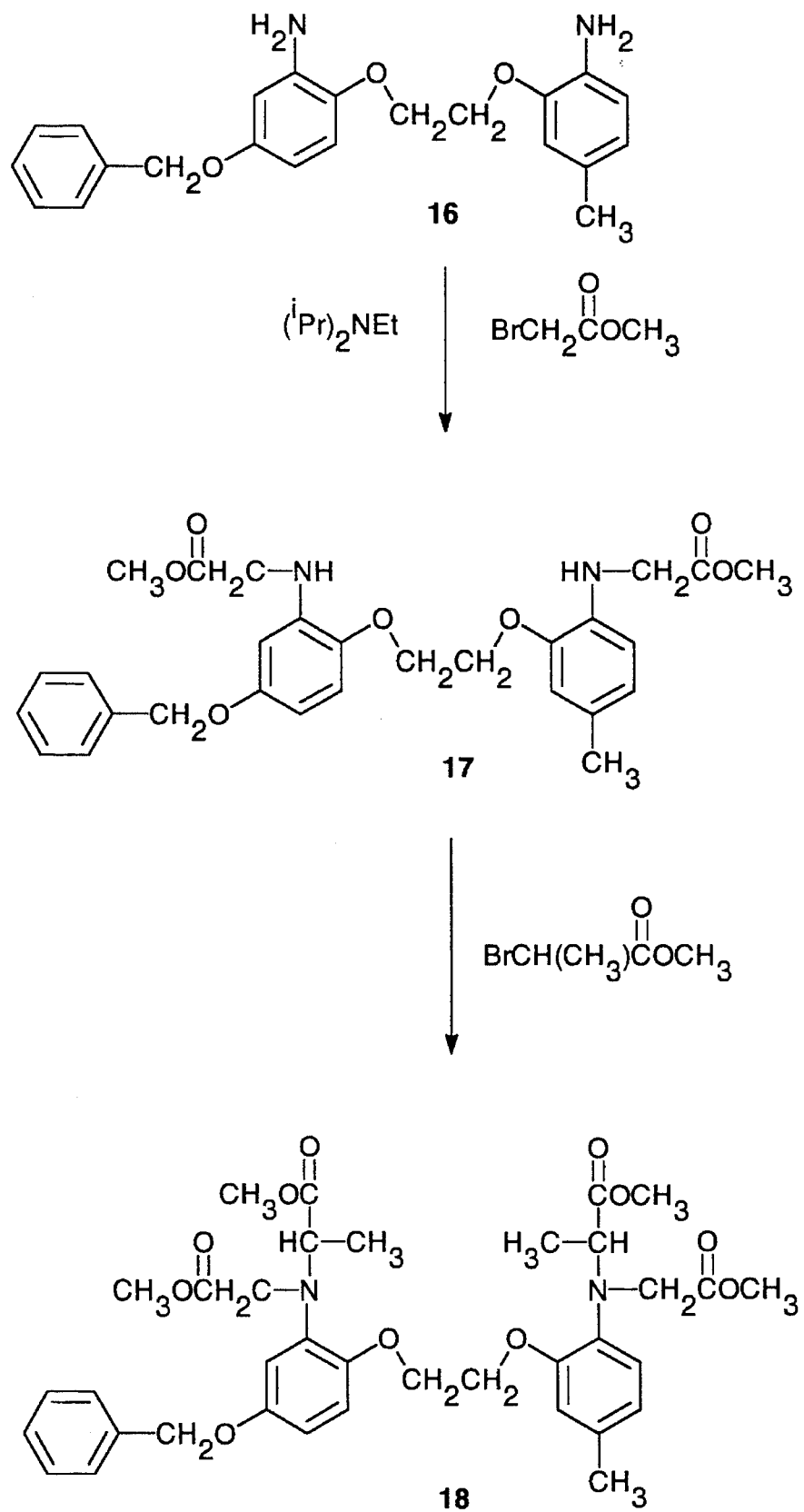
FIG. 8: Synthetic scheme for preparation of Compounds 17 and 18, as described in Examples 13 and 14.
Figure 9:
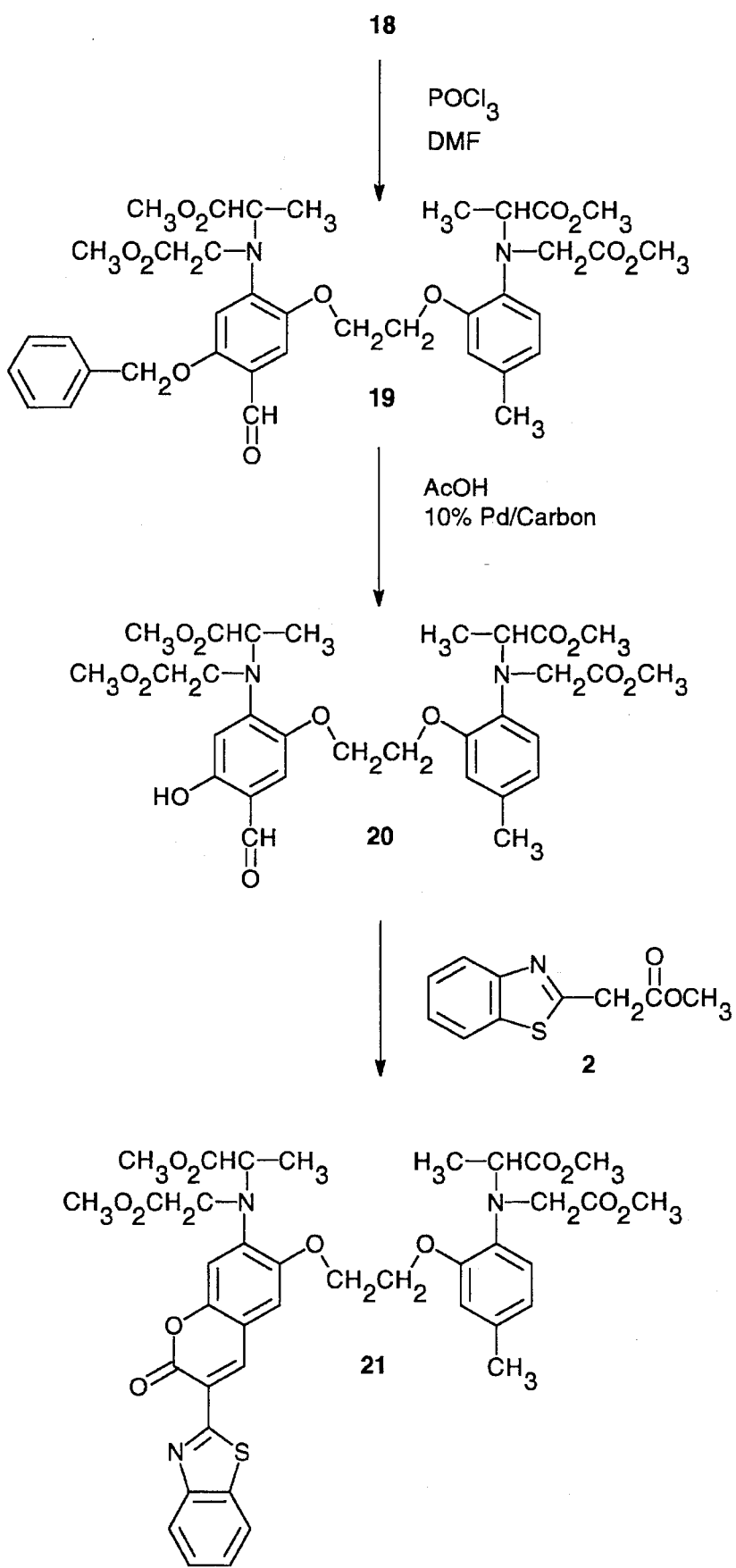
FIG. 9: Synthetic scheme for preparation of Compounds 19, 20 and 21, as described in Examples 15, 16 and 17.
Figure 10:
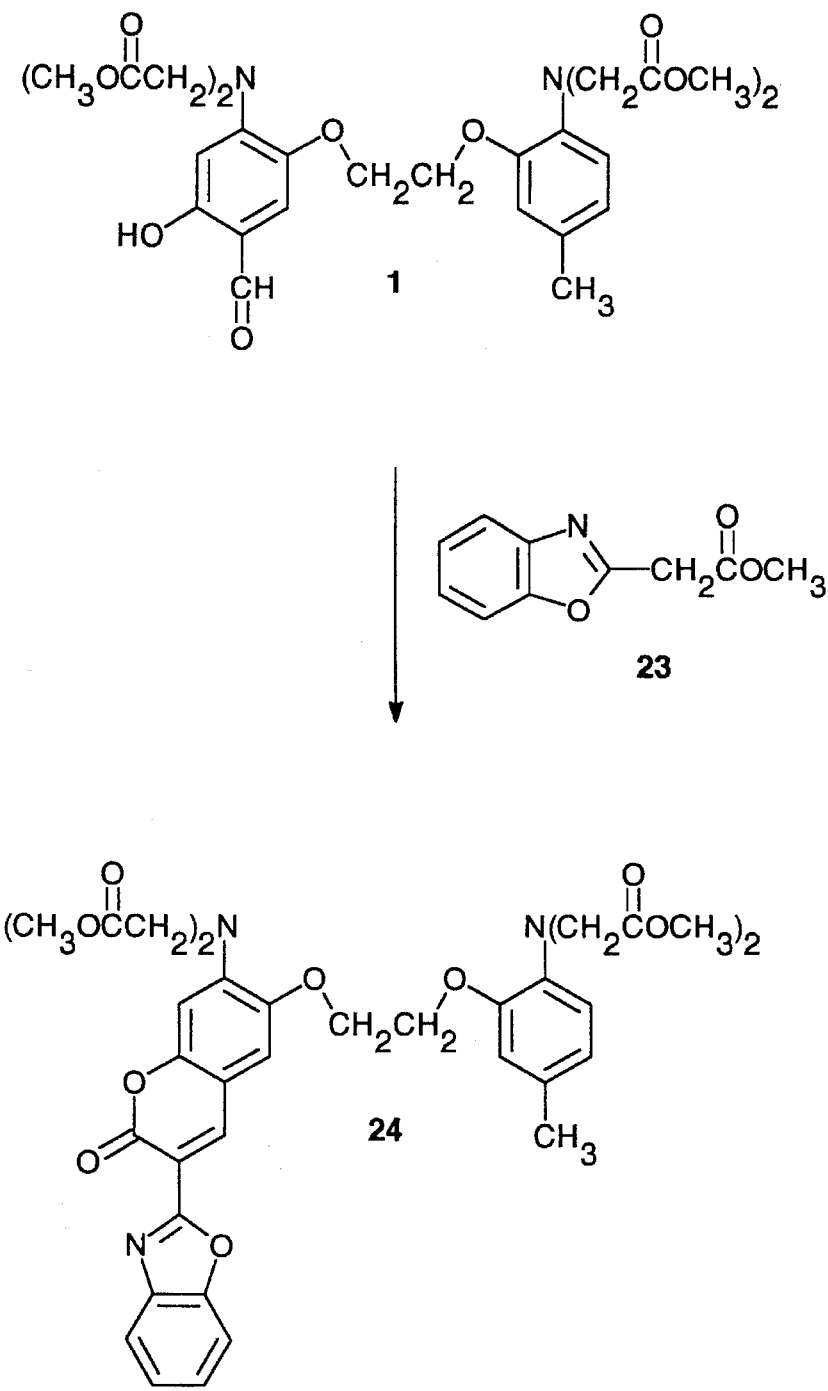
FIG. 10: Synthetic scheme for preparation of Compound 24, as described in Example 19.

Introduction of a methyl group on the iminodiacetic acids involved in metal chelation has the effect of increasing the affinity of the BAPTA chelate for $Ca^{2+}$ (Smith et. al., supra). This method for varying $Ca^{2+}$ affinity can be utilized to make coumarin-based $Ca^{2+}$ indicators with a range of affinities for free $Ca^{2+}$. As shown in Examples 13–4, two methyl groups can be introduced next to the chelating acids by two sequential alkylations. The diamine (16) is reacted with two equivalents of methyl bromoacetate to give the bis-methyl ester (17), which is isolated and treated with methyl 2-bromopropionate at a higher temperature in the presence of a stronger base to give the tetraester (18) (FIG. 8). Modifications of this strategy can give one, two, three or four methyl groups on the iminodiacetic acid groups of the BAPTA chelator, resulting in a series of indicators with increased affinity for $Ca^{2+}$ when compared with the parent indicator, BTC BAPTA. As shown for similar compounds (Tsien et al., BIOCHEMISTRY, supra), electron withdrawing groups (e.g. bromo) at the 5' position of the BAPTA chelator (para to the amino nitrogen) can lower the ion binding affinity of the indicator. Appropriate substitution at the 5' position can therefore yield a series of indicators with decreased affinities for $Ca^{2+}$ when compared to the parent indicator. A combination of these strategies can be used to fine-tune the $Ca^{2+}$ affinity across a wide range of free $Ca^{2+}$ concentrations.

Method of Use

In order for a compound of the present invention to be useful as an indicator, the fluorescent properties of the chelator must exhibit some change upon complexation of the desired metal ion in the carboxylate chelate. The instant compounds display a shift in either excitation or emission energy upon the complexation of a $Ca^{2+}$ ion.

The specific indicator used in an assay or experiment is selected based on the desired affinity for the target ion as determined by the expected concentration range in the sample, the desired spectral properties, and the desired selectivity as described above. Initially, the suitability of a material as an indicator of ion concentration is commonly tested by mixing a constant amount of the indicating reagent with a measured amount of the target ion under the expected experimental conditions.

Preferred indicators display a high selectivity, that is, they show a high rejection of non-target ions. The interference of a non-target ion can be tested by a comparable titration of the indicator with that ion. Although $Ca^{2+}$ is the preferred target ion, any ion that yields a detectable change in absorption wavelengths, emission wavelengths, fluorescence lifetimes or other measurable optical property over the concentration range of interest can potentially be measured using one of the indicators of this invention.

The indicator is generally prepared for use as a detection reagent by dissolving the indicator in solution at a concentration that is optimal for detection of the indicator at the expected concentration of the target ion. Modifications that are designed to enhance permeability of the indicator through the membranes of living cells, such as acetoxymethyl esters and acetates, may require the indicator to be predissolved in an organic solvent such as dimethylsulfoxide (DMSO) before addition to a cell suspension, where the indicators then readily enter the cells. Intracellular enzymes cleave the esters to the more polar acids and phenols that are then well retained inside the cells.

The optical response of the indicating reagent is determined by changes in absorbance or fluorescence, preferably fluorescence. If absorbance measurements are used to determine ion concentrations, then it is usually optimal to adjust the optical density of the indicator in the sample over the range of analyte concentration to a value of approximately 0.02 to 2.5 (most preferably 0.1 to 1). For fluorescence measurements, the concentration of the indicator will depend mostly on the sensitivity of the equipment used for its detection.

If the optical response of the indicator will be determined using fluorescence measurements, sample are typically stained with indicator concentrations of $10^{-9}$M to $10^{-4}$M. The most useful range of analyte concentration is about one log unit above and below the dissociation constant of the ion-indicator complex. This dissociation constant is determined by titration of the indicator with a known concentrations of the target ion, usually over the range of virtually zero concentration to approximately 100 millimolar of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects need to be taken into account when calibrating an indicator.

The indicator is combined with a sample in a way that will facilitate detection of the target ion concentration in the sample. The sample is generally a fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; and in chemical reactors.

Quantification of metal ion levels in samples is accomplished using the indicators of the present invention by ratiometric methods known in the art (Haugland, HANDBOOK OF FLUORESCENT PROBES AND RESEARCH CHEMICALS, 1992, pp., 111–112). The ratiometric method provides accurate measurement of ion concentrations by the treatment of the fluorescence data as the ratio of excitation or fluorescence intensities at two wavelengths, rather than the absolute intensity at a single wavelength. Using the ratio method, a number of variables that may perturb the ion concentration measurements are eliminated. In particular, ion-dependent factors that affect the signal intensity, such as nonuniform intracellular dye concentrations, probe leakage, dye bleaching and cell thickness, are canceled in the ratio measurements, since these parameters have a similar effect on intensities at both wavelengths. While the ratio method can be used to determine concentrations using observation of either the excitation spectra of the indicator, the emission spectra of the indicator, or both, in the case of the indicators of the present invention, the shift in excitation energy upon binding metal ions makes observation of the excitation spectrum a more useful technique. In either case, to achieve maximal utility, the indicator must be calibrated (to compensate for variance in the dissociation constant of the indicator due to ionic strength, viscosity, or other conditions within the cell). To calibrate the indicator, ionophores such as A-23 187 or ionomycin are used. Non-ratiometric analysis can also be accomplished by calibration with a second fluorescent dye present in the sample.

Typically, embodiments of the invention display a shift in excitation maxima upon metal ion binding of greater than about 20 nm, preferably greater than about 30 nm, and more preferably greater than about 40 nm. The absolute wavelength of excitation maxima are typically at wavelengths greater than about 400 nm.

The optical response of the indicator to the ion can be detected by various means that include measuring absorbance or fluorescence changes with an instrument, visually, or by use of a fluorescence sensing device. Several examples of fluorescence sensing devices are known, such as fluorometers, fluorescence microscopes, laser scanners, and flow cytometers as well as by cameras and other imaging equipment. These measurements may be made remotely by incorporation of the fluorescent ion sensor as part of a fiber optic probe. The indicator may be covalently attached to the fiber optic probe material, typically glass or functionalized glass (e.g., aminopropyl glass) or the indicator may be attached to the fiber optic probe via an intermediate polymer, such as polyacrylamide. The indicator solution may alternatively be incorporated non-covalently within a fiber optic probe, as long as there is a means whereby the target ion can come into contact with the indicator solution.

The examples below are given so as to illustrate the practice of this invention. They are not intended to limit or define the entire scope of the invention.

EXAMPLE 1

Preparation of BTC BAPTA, tetramethyl ester (3)

4-hydroxy-5-methyl-4-formyl BAPTA tetramethyl ester (1) (200 mg, 0.34 mmol; Compound XXVI in U.S. Pat. No. 4,603,209 to Tsien et al., supra) is added to a solution of methyl α-benzothiazolyl acetate (2) (90 mg, 0.43 mmol; Iatridou et al., supra) in 3 mL methanol and 1 μL piperidine. The resulting solution is heated for one hour at 70° C., then cooled to 0° C. The resulting yellow precipitate was filtered and washed with 10 mL diethyl ether to give 240 mg (95%) of 3 (m.p.: 200°–207° C.). $^1$H NMR (d$_6$-DMSO): δ=9.14 (s, 1H); 7.63 (s, 1H); 7.56–7.44 (m, 2H); 6.78–6.64 (m, 4H); 6.16 (d, 1H); 6.02 (d, 1H); 4.33 (s, 4H); 4.25 (s, 2H); 4.22 (s, 2H); 4.07 (s, 4H); 3.53 (s, 6H); 3.49 (s, 6H); 2.23 (s, 3H). IR (cm$^{-1}$): 1750, 1710, 1742, 1201, 1165, 771.

Elemental analysis based on $C_{37}H_{37}N_3SO_{12}$ ((Calc.) Found): C (59.43) 60.05; H (4.99) 4.91; N (5.62) 5.68; S (4.29) 4.6.

EXAMPLE 2

Preparation of BTC BAPTA tetraacetic acid (4)

Compound 3 (50 mg, 0.07 mmol) is dissolved in 3 mL acetonitrile and LiI (300 mg, 2.24 mmol) is added in one portion. The resulting suspension is heated to reflux for 96 hours. After cooling, the resulting orange precipitate is filtered and washed with 3 mL acetonitrile and 5 mL acetone to give the tetralithium salt. The lithium salt is dissolved in 5 mL deionized water and the solution is acidified to pH 4 using 3M HCl. The resulting orange solid is centrifuged and dried under vacuum to give pure 4 (95% yield). $^1$H NMR (d$_6$-DMSO): δ= 9.09 (s, 1H); 8.03 (d, 1H); 7.50–7.42 (m, 4H); 6.8 (s, 1H); 6.75–6.60 (m, 4H); 4.29 (s, 4H); 4.26 (s, 4H); 4.03 (s, 4H); 2.22 (s, 3H). IR (cm$^{-1}$): 1725, 1618, 1410, 1247, 771.

EXAMPLE 3

Preparation of BTC BAPTA, tetraacetoxymethyl ester (5)

Compound 4 (50 mg, 0.072 mmol) is dissolved in 5 mL acetonitrile and diisopropylethylamine (46 mg, 0.36 mmol) is added. The solution is stirred for 30 minutes followed by the addition of bromomethyl acetate (0.11 gm, 0.7 mmol) in one portion. The reaction is stirred for 2 hours at room temperature, after which the solvent is removed under reduced pressure. The resulting orange oil is suspended in 10 mL ethyl acetate and washed with 15 mL deionized water and 15 mL saturated NaCl. The organic layer is dried over $Na_2SO_4$ and evaporated under reduced pressure. The compound is further purified by column chromatography (40–60 µm $SiO_2$), eluting with a 1:1 ethyl acetate:hexanes. Column fractions containing pure 5 are combined and dried in vacuo to give 5 as a pure solid (75% yield). $^1H$ NMR ($CDCl_3$): δ=8.96, (s, 1H);, 8.03–7.92 (m, 2H); 7.51–7.48 (m, 2H); 6.94 (s, 1H); 6.8–6.65 (m, 4H); 5.63 (s, 4H); 5.61 (s, 4H); 4.29 (s, 4H); 4.24 (s, 4H); 4.11 (s, 4H); 2.23 (s, 3H); 2.06 (s, 12H).

EXAMPLE 4

Preparation of Cyano-BTC BAPTA, tetramethyl ester (6)

Compound 3 (10 mg, 0.0134 mmol) is dissolved in 1 mL dry DMF and 0.1 mL of a 15 mg/mL solution of KCN (1.5 mg, 0.027 mmol) is added in one portion. The solution is stirred at 35° C. for 90 minutes, diluted with 5 mL chloroform and then irradiated for 5 minutes using a 275 W sunlamp. The light yellow mixture is oxidized to a dark red solution. Analysis using thin layer chromatography showed complete conversion of 3 to a red fluorescent product having a lower $R_f$. The product is further purified by column chromatography on silica gel (100 mL wet bed volume) eluting with 2:1 ethyl acetate: hexanes. Fractions containing pure product are evaporated under reduced pressure to give a red oil.

EXAMPLE 5

Preparation of Cyano-BTC BAPTA, tetralithium salt (7)

Compound 6 (25 mg, 0.032 mmol) is dissolved in 3 mL dry acetonitrile and LiI (0.21 g, 1.6 mmol) is added in one portion. The red suspension is heated at reflux for 72 hours until the hydrolysis is complete as determined using thin layer chromatography. The reaction mixture is then cooled to 0° C. and centrifuged to give pure 7 as a red solid. The pellet is redissolved in water and purified using column chromatography on Sephadex® LH-20 eluting with pH 7.5 LiOH in deionized water. The product elutes as a red band, which is lyophilized to give 7 as a red powder (12 mg, 51% yield).

EXAMPLE 6

Preparation of 1,2-bis-(2-nitro-4-benzyloxyphenoxy)ethane (9)

Compound 8 (50 g, 0.204 mole) (Compound XX U.S. Pat. No. 4,603,209 to Tsien et al. supra) is dissolved in 200 mL DMF and $K_2CO_3$ (80 g, 57.9 mmol) is added. The red suspension is stirred at 45° C. for 30 minutes followed by the addition of dibromoethane (21 g, 0.112 mole) in one portion. The reaction temperature is raised to 125° C. for three hours until complete consumption of the bright yellow 8 as determined using thin layer chromatography (eluting with 3:1 $CHCl_3$:ethyl acetate) with formation of a colorless product with a lower $R_f$. The reaction mixture is poured into 1 L deionized water and the resulting precipitate is filtered and resuspended in 500 mL methanol. The suspension is stirred for two hours and then filtered and dried to give 9 (41 g, 80%).

EXAMPLE 7

Preparation of 1,2-bis-(2-amino-4-benzyloxyphenoxy)ethane (10)

Compound 9 (40 g, 77.5 mmol) is dissolved in 400 mL of $CH_2Cl_2$ and 1.5 g 5% platinum on charcoal is added. The reaction is shaken under 40 psi $H_2$ for six hours until the reaction is judged complete using thin layer chromatography (1:9 methanol:chloroform). The product reacts with ninhydrin on a TLC plate to give a ruddy brown product with an $R_f$ of 0.3. The reaction mixture is filtered through diatomaceous earth to remove the catalyst, and the resulting filtrate is evaporated under reduced pressure. The resulting semi-crystalline oil is stirred with 400 mL methanol for two hours while protected from light. The resulting light gray crystals are filtered and dried to give 10 in 90% yield.

EXAMPLE 8

Preparation of 1,2-bis-(2-amino-4-benzyloxyphenoxy)ethane-N,N,N',N'-tetraacetic acid tetramethyl ester (11)

Compound 10 (22 g, 48.2 mmol) is dissolved in 200 mL dry acetonitrile. Diisopropylethylamine (34.2 g, 0.265 moles) is added, followed by NaI (9.4 g, 62.7 mmol) and methyl bromoacetate (40.6 g, 0.265 mole). The suspension is stirred and heated to reflux for 36 hours. Thin layer chromatography shows greater than 90% conversion to a lower $R_f$ product that reacts with potassium dichromate solution on a TLC plate to give a deep purple product. The reaction mixture is condensed under reduced pressure to give a thick oil, which is redissolved in ethyl acetate. The suspension is filtered to remove insoluble salts, and the ethyl acetate filtrate is washed with 300 mL deionized water and 300 mL saturated NaCl. The organic layer is dried over $Na_2SO_4$ and evaporated under reduced pressure to give a tan oil. After crystallization from 500 mL methanol and drying, 18 g 11 (51% yield) is collected.

EXAMPLE 9

Preparation of 1,2-bis-(2-amino-4-benzyloxy-5-formylphenoxy)ethane, N,N,N'N'-tetraacetic acid tetramethyl ester (12)

Compound 11 (5 g, 6.7 mmol) is dissolved in 30 mL DMF and cooled to 0° C. under nitrogen. In a separate flask, 15 mL DMF is cooled to 0° C. and $POCl_3$ (3.6 g, 27 mmol) is added dropwise over 15 minutes. The reaction mixture is stirred at room temperature for 30 minutes. The $POCl_3$/DMF complex is added to the solution of Compound 11 over 20 minutes. The reaction mixture is stirred at room temperature for 10 hours. Analysis of the yellow suspension by thin layer chromatography (1:1 ethyl acetate:hexanes) shows complete conversion of 11 to a slightly fluorescent blue product that has a lower $R_f$. The reaction mixture is poured into 500 mL deionized water with stirring, and the pH is adjusted to 7.5 using a 5% KOH solution. Ethyl acetate (400 mL) is added, and the organic layer is collected. The organic layer is washed with 400 mL of water and 400 mL of saturated NaCl, then dried over $Na_2SO_4$ and evaporated to a yellow solid. The solid is resuspended in 150 mL methanol and filtered to give 4.6 g (85% yield) of Compound 12 as a colorless powder, pure by thin layer chromatography (1:2 ethyl acetate:hexanes).

EXAMPLE 10

Preparation of
1,2-bis-(2-amino-5-formyl-4-hydroxyphenoxy)ethane,
N,N,N'N'-tetraacetric acid tetramethyl ester (13)

Compound 12 (1.5 g, 1.87 mmol) is dissolved in 40 mL glacial acetic acid in a 500 mL Parr hydrogenation flask and approximately 0.1 g 10% palladium on charcoal is added. The reaction is shaken under 40 p.s.i. hydrogen pressure for four hours until analysis using thin layer chromatography shows complete conversion to a slightly green fluorescent product that elutes with an $R_f$ of 0.5 in a 1:1 mixture of ethyl acetate:hexanes. The reaction mixture is filtered through diatomaceous earth and the brown acetic acid filtrate is evaporated under reduced pressure to a tan oil. The oil is dissolved in 15 mL $CHCl_3$ and purified on a silica gel column eluting with 1:1 ethyl acetate:hexanes. Fractions containing pure product are combined and evaporated under reduced pressure to a give 13 as a colorless solid (920 mg, 79% yield).

EXAMPLE 11

Preparation of bis-BTC BAPTA tetramethyl ester (14)

Compound 13 (75 mg, 0.056 mmol) is dissolved in 5 mL methanol with piperidine and Compound 2 (110 mg) is added in one portion with stirring. The reaction is heated to 70° C. for one hour, cooled to 0° C. and centrifuged. The pellet is resuspended three times in diethyl ether, centrifuged and dried to give a yellow powder that is pure by thin layer chromatographic analysis using ethyl acetate.

EXAMPLE 12

Preparation of Bis-BTC BAPTA, tetralithium salt (15)

Compound 14 (50 mg, 0.056 mmol) is dissolved in 5 mL dry acetonitrile and LiI (0.37 g, 2.7 mmol) is added in one portion with stirring. The reaction mixture is heated at reflux for 70 hours until the hydrolysis is determined to be complete by thin layer chromatography (10:10:2:0.2 chloroform:methanol:water:acetic acid). The highly fluorescent reaction mixture is filtered and the resulting solid is redissolved in 3 mL deionized water. The aqueous dye solution is purified on lipophilic Sephadex® LH-20 column (100 mL wet bed volume) eluting with pH 7.5 LiOH in deionized water. The product elutes cleanly as a yellow fluorescent band. The product band is collected, then frozen and lyophilized to give Compound 15 as a bright yellow powder (20 mg).

EXAMPLE 13

Preparation of
1-(2-amino-4-benzyloxyphenoxy)-2-(2'-amino-5'-methylphenoxy)ethane, N,N'-diacetic acid, dimethyl ester (17)

Compound 16 (25 g, 68.7 mmol) (Compound XXIII in U.S. Pat. No. 4,603,209 to Tsien et al. supra) is dissolved in 100 mL dry acetonitrile. Diisopropylethylamine (22.2 g, 0.172 mole) is added in one portion, followed by methyl bromoacetate (22.6 g, 0.147 mole). The tan suspension is heated at reflux with stirring for 10 hours until all of the starting amine is consumed. The reaction mixture is then diluted with 200 mL ethyl acetate and the reaction is filtered to remove salts. The organic filtrate is evaporated under reduced pressure and crystallized from 200 mL hot methanol to give 22 g (43.3 mmol) Compound 17 (63 % yield). $^1H$ NMR in $CDCl_3$ is consistent with mono-alkylation of the nitrogens on both rings.

EXAMPLE 14

Preparation of
1-(2-amino-4-benzyloxyphenoxy)-2-(2'-amino-5'-methylphenoxy)ethane, N,N' -diacetic
acid-N,N'-di(d-methylacetic acid) tetramethyl ester (18)

Compound 17 (18 g, 35.4 mmol) is dissolved in 80 mL DMF. Methyl D-2-bromopropionate (7.2 g, 43.2 mmol) is added in one portion, followed by 1,8-bis-dimethylaminonaphthalene (Proton Sponge®) (9.25 g, 43.2 mmol). The suspension is heated to 120° C. for 15 hours. Analysis by thin layer chromatography (1:1 ethyl acetate:hexanes) reveals one major product with an $R_f$ of 0.6. The reaction mixture is then diluted with 400 mL ethyl acetate and washed twice with 2% phosphoric acid, then once with saturated NaCl. The organic layer is dried over $Na_2SO_4$ and evaporated under reduced pressure to give a brown oil that is purified on a silica gel column eluting with 1:1:1 ethyl acetate:chloroform:hexanes. Fractions containing pure product are combined and evaporated under reduced pressure to give Compound 18 as a colorless solid.

EXAMPLE 15

Preparation of
1-(2-amino-4-benzyloxy-5-formylphenoxy)-2-(2'-amino-5'-methylphenoxy)ethane, N,N'-diacetic
acid-N,N'-dipropionic acid, tetramethyl ester (19)

Compound 18 (9 g, 13.2 mmol) is dissolved in 40 mL dry DMF and cooled to 0° C. $POCl_3$ (5.3 g, 39.7 mmol) is added dropwise over 20 minutes and the reaction mixture is stirred at room temperature for 24 hours. The brown solution is added to 500 mL water and the resulting white precipitate is collected by filtration. The crude product is redissolved in 100 mL of ethyl acetate and washed three times with 100 mL saturated NaCl. The organic layer is evaporated under reduced pressure to a light yellow oil that is stirred with 75 mL methanol and filtered to give Compound 19 as a light yellow solid (8.2 g, 87% yield), that is pure by thin layer chromatography (1:1 ethyl acetate:hexanes).

EXAMPLE 16

Preparation of
1-(2-amino-5-formyl-4-hydroxyphenoxy)-2-(2'-amino-5'-methylphenoxy)ethane, N,N' -diacetic
acid-N,N'-dipropionic acid, tetramethyl ester (20)

Compound 19 (6 g, 8.47 mmol) is dissolved in 40 mL glacial acetic acid and approximately 0.5 g 10% palladium on carbon is added. The reaction is shaken under 40 psi hydrogen pressure for two hours. When the reaction is complete by thin layer chromatography, the reaction mixture is filtered through diatomaceous earth to remove the catalyst, and the filtrate is evaporated under reduced pressure to give Compound 20 as a tan oil. Crystallization from 80 mL hot methanol gives a colorless powder (4.5 g, 85% yield).

EXAMPLE 17

Preparation of dimethyl-BTC BAPTA, tetramethyl ester (21)

Compound 20 (1.2 g, 1.9 mmol) is dissolved in 7 mL methanol and piperidine (25 µL) is added with stirring together with Compound 2. The reaction mixture is heated to 45° C. and formation of the highly fluorescent product is monitored by thin layer chromatography eluting with 1:1 ethyl acetate: hexanes. When the reaction is complete, the reaction mixture is evaporated under reduced pressure, and the resulting yellow solid is dissolved in 3 mL chloroform and purified on a silica gel column (150 mL wet bed volume) eluting with 20 % ethyl acetate in chloroform. Column fractions containing pure compound are combined and evaporated under reduced pressure to give 21 as a yellow oil.

EXAMPLE 18

Preparation of dimethyl-BTC BAPTA, tetralithium salt (22)

Compound 21 (50 mg, 0.064 mmol) is dissolved in 5 mL dry acetonitrile and LiI (0.59 g, 4.5 mmol) is added. The reaction is heated at reflux for 48 hours. The resulting orange suspension is then centrifuged to give the crude product as a dark orange pellet. The pellet is dissolved in 2 mL deionized water and purified on lipophilic Sephadex® LH-20 (100 mL wet bed volume) eluting with pH 7.5 LiOH. The fluorescent product is frozen and lyophilized to give 22 as a yellow powder.

EXAMPLE 19

Preparation of BOC BAPTA, tetramethyl ester (24)

Compound 1 (230 mg, 0.39 mmol; Compound XXVI in U.S. Pat. No. 4,603,209 to Tsien et al., supra) is dissolved in 3 mL dry methanol and 3 µL piperidine. Ethyl α-benzoxazolyl acetate 23 (100 mg, 0.49 mmol, Iatridou, H. et. al.) is added in one portion and the reaction heated to reflux for 60 minutes. The reaction is cooled to 0° C., filtered and washed with 10 mL diethyl ether to give 210 mg Compound 24 (81% yield). NMR (CDCl$_3$): δ=8.68 (s, 1H); 7.85–7.82 (m, 1H); 7.61–7.59 (m, 1H); (m, 1H); 7.38–7.36 (m, 2H); 7.05 (s, 1H); 6.78 (d, 1H); 6.71 (d, 1H); 6.67 (d, 1H); 6.63 (s, 1H); 4.29 (s, 2H); 4.26 (s, 4H); 4.25 (s, 2H); 4.13 (s, 4H); 3.63 (s, 6H); 3.60 (s, 6H); 2.27 (s, 3H). IR (cm$^{-1}$); 1755, 1738, 1193, 1183. FAB-MS m/z=732 (M+1)$^+$.

EXAMPLE 20

Preparation of BOC BAPTA, tetralithium salt (25)

Compound 24 (100 mg, 0.13 mmol) is dissolved in 5 mL dry acetonitrile and LiI (1.0 gm, 7.5 mmol) is added in one portion. The suspension is stirred at reflux under nitrogen atmosphere for 96 hours. The reaction is then filtered and the isolated light yellow tetralithium salt is dissolved in 2 mL deionized water and purified on lipophilic Sephadex® LH-20 (100 mL wet bed volume) eluted with pH 7.5 LiOH. Column fractions containing pure product are combined, frozen and lyophilized give 25 as a yellow powder.

EXAMPLE 21

Determination of the Ca$^{2+}$ Binding Constant of Compound 4

Compound 4 is dissolved in 1 mL 10 mM MOPS water to give a final dye concentration of approximately 1 mM. This is diluted to a final concentration of 1 µM in a series of Ca$^{2+}$ buffers containing 0.1M KCl and 10 mM MOPS buffer at pH 7.20 as originally described by Tsien (BIOCHEMISTRY, supra). The curves shown in FIG. 1 represent the change in excitation ratio as Ca$^{2+}$ levels vary from approximately 1.3 µM to 100 µM. These buffers have added Ca$^{2+}$ in the micromolar range; the Ca$^{2+}$ concentration for 100 mM KCl and 10 mM MOPS at pH 7.20 was determined with the Ca$^{2+}$ selective indicator fura-2 as follows: fura-2, pentapotassium salt (Molecular Probes, Inc. Eugene Oreg.) is diluted to a final concentration of 1 µM in 11 EGTA-buffered free Ca$^{2+}$ concentrations ranging from "zero Ca$^{2+}$" (10 mM EGTA) to 39.4 µM free Ca$^{2+}$ (Ca$^{2+}$ Calibration Buffer Kit II, Molecular Probes, Eugene Oreg.). The excitation spectra of the solutions are scanned from 300 nm to 500 nm, collecting the emission at 510 nm to generate a family of curves with a clear isosbestic point. The ratio of the absorbance at 340 nm to the absorbance at 370 nm is measured and the resulting ratio is plotted against the concentration of Ca$^{2+}$ to generate a linear calibration curve. Fura-2 (1 µM) is then diluted into 2 mL of 100 mM KCl and 10 mM MOPS at pH 7.20. The excitation spectra are scanned and the resulting 340/370 ratio is used to calculate a value of 1.3 µM free Ca$^{2+}$ for the lowest Ca$^{2+}$ concentrations. An overlay of the spectra of 1 µM fura-2 in 100 mM KCl, 10 mM MOPS and 1 µM fura-2 in 1.3 µM of Ca$^{2+}$ shows that they are identical. An additional 1.3 µM of Ca$^{2+}$ is then added to the concentrations of all the micromolar buffers for the determination of the dissociation constant.

EXAMPLE 22

Detection of Ca$^{2+}$ in 3T3 Mouse Fibroblasts with Compound 5

The cell line NIH 3T3 (mouse fibroblasts) is used. Cells on coverslips are incubated with 1 and 10 µM of 5 at room temperature for 25 minutes. The loading medium used is Dulbecco's Modified Eagle Medium (DMEM); cells are incubated without fetal calf serum. After incubation, the cells are washed twice in PBS containing 1 mM CaCl$_2$ and 1 mM MgCl$_2$. A long pass fluorescein filter is used to view the cells, which appear evenly stained and are greenish yellow in color. The same solution of PBS is used to prepare a 10 µM solution of the Ca$^{2+}$ ionophore 4-bromo A-23187. A coverslip of cells loaded with 1 µM and one with 10 µM dye are treated for 10 minutes with the ionophore solution. The resultant staining of cells is a more blue shade of green and the fluorescence intensity of the cells is higher after ionophore treatment. The change in intensity is much more noticeable than the change in color.

EXAMPLE 23

Fluorescence Measurements of BTC, AM in Mouse Myeloma P3X Cells

Figure 2:
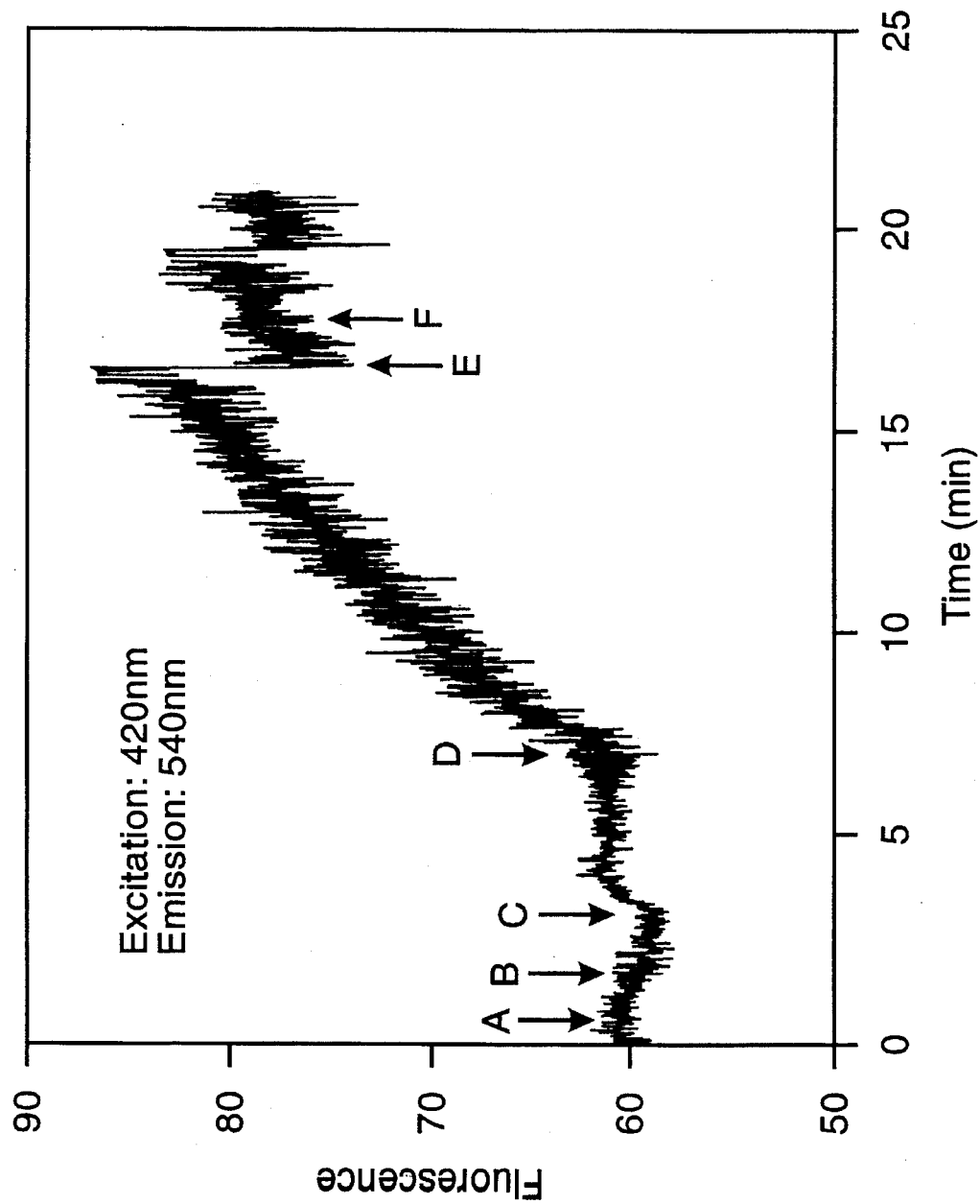
FIG. 2: The time course of the intracellular $Ca^{2+}$ response of Compound 5 for 30 minutes after loading in cells, as described in Example 23. Additions are as follows: (A) 10 µM $MnCl_2$; (B) 10 mM $CaCl_2$; (C) 10 µM 4-BrA23187; (D) 0.1% saponin; (E) 40 µM $MnCl_2$.

Mouse myeloma P3X63-Ag8.653 cells are incubated with 1 μM Compound 5 for 30 minutes at room temperature in Dulbecco's Modified Eagle Medium (D-MEM). The cells are spun down and washed twice in HEPES-buffered saline (120 mM NaCl, 5 mM KCl, 1 mM $MgCl_2$, 1 mM $CaCl_2$, 10 mM HEPES, pH 7.4) then resuspended in this buffer at a concentration of approximately $10^6$ cells/mL. Three mL of this cell suspension are transferred to a quartz cuvette with a magnetic spin bar for fluorescence measurements in a PTI Alphascan fluorometer equipped with a 75 W xenon short arc lamp. All slit widths are set to 4 nm; the excitation wavelength used is 420 nm and emission is monitored at 540 nm (FIG. 2). To quench any dye that might leak from the cells during the course of the experiment, 10 μM $MnCl_2$ is added (A). Solution calcium levels are next elevated to 10 mM by the addition of $CaCl_2$ (B); this high amount is required to enhance calcium transport of the ionophore (necessary dye to the low $K_d$ of the indicator). 10 μM 4-BrA23187 is added (C); as can be seen, this results in only a small change in intracellular calcium levels. To further increase cellular $Ca^{2+}$ levels, 0.1% saponin is added (FIG. 2, point D). Manganese chloride additions to a final concentration of 50 mM (FIG. 2, points E and F) result in only a small reduction in fluorescence intensity.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula:

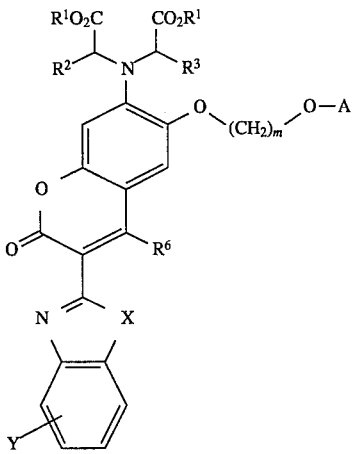

wherein m is either 2 or 3;

A is either of the formula

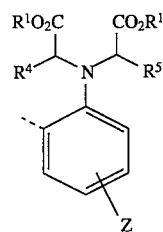

or A is of the formula

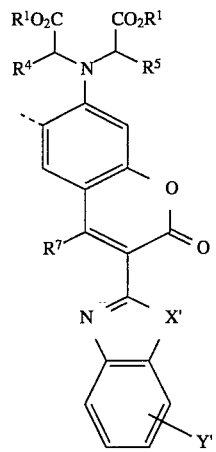

wherein $R^1$ is H, an alkyl group having 1–5 carbons, a benzyl, an alpha-acyloxyalkyl or a pharmaceutically acceptable esterifying group, a t-butyldimethylsilyl ester, or a pharmaceutically acceptable salt;

$R^2$, $R^3$, $R^4$ and $R^5$ are independently H or methyl;

$R^6$ and $R^7$ are independently H, CN, $CH_3$, $CF_3$ or $CONH_2$;

X and X' are independently O, S, or $C(CH_3)_2$;

Y and Y' are independently H, an alkyl having 1–18 carbons, $—NO_2$, $—NH_2$, $—NH(C=O)(CH_2)_nCH_3$, $—CF_3$, F, Cl, Br, I, $—OR^8$, $—CO_2R^9$, or $—OCH_2CO_2R_9$, where n=0–16; $R^8$ is H, an alkyl group having 1–18 carbons, a benzyl ($C_6H_5CH_2—$), an alpha-acyloxyalkyl, acetate, or a t-butyldimethylsilyl ether; and $R^9$ is H, an alkyl group having 1–17 carbons, a benzyl ($C_6H_5CH_2—$) an alpha-acyloxyalkyl or other pharmaceutically acceptable esterifying group, a t-butyldimethylsilyl ester, or a pharmaceutically acceptable salt; or one of Y and Y' is a covalently attached conjugant; and Z is one of H, an alkyl having 1–18 carbons, $—NH_2$, $—NH(C=O)(CH_2)_nCH_3$, $—CF_3$, F, Cl, Br, I, $—OR^8$, $—CO_2R^9$, or $—OCH_2CO_2R^9$; or Z is a covalently attached conjugant.

2. A compound as claimed in claim 1, wherein one of Y, Z and Y' is a covalently attached conjugant.

3. A compound as claimed in claim 2, wherein said covalently attached conjugant is a polymer film, a polymer microparticle, a dextran, or glass.

4. A compound as claimed in claim 1, of the formula

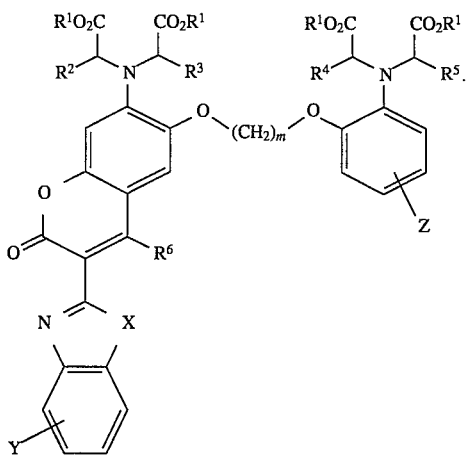

5. A compound as claimed in claim 4, wherein m=2.

6. A compound as claimed in claim 4, wherein $R^1$ and $R^9$ are acetoxymethyl esters, or $R^1$ is an acetoxymethyl ester and Y is H.

7. A compound as claimed in claim 4, wherein X is O or S.

8. A compound as claimed in claim 4, wherein $R^2$, $R^3$, $R^4$ and $R^5$ are each H.

9. A compound as claimed in claim 4, wherein $R^6$ is H or CN.

10. A compound as claimed in claim 1, of the formula

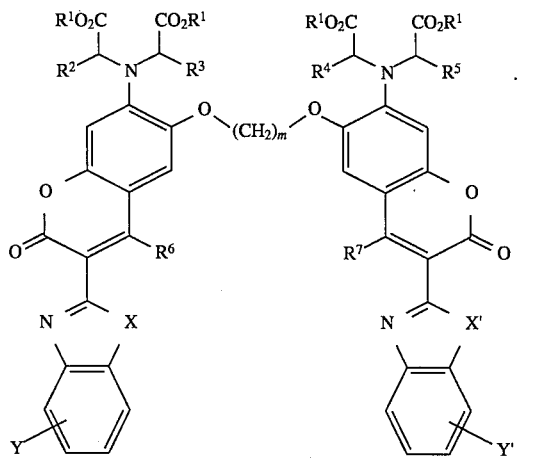

11. A compound as claimed in claim 10, wherein m=2.

12. A compound as claimed in claim 10, wherein $R^2$, $R^3$, $R^4$ and $R^5$ are each H.

13. A compound as claimed in claim 10, wherein $R^6$ is H or CN.

14. A compound as claimed in claim 10, wherein $R^1$ and $R^9$ are acetoxymethyl esters, or $R^1$ is an acetoxymethyl ester and Y is H.

15. A compound as claimed in claim 10, wherein X is or S.

16. A method of measuring the concentration of a polycationic metal ion in a sample, comprising:

a) adding to said sample, in an amount sufficient to generate a detectable fluorescent response to said metal ion, a compound according to the formula

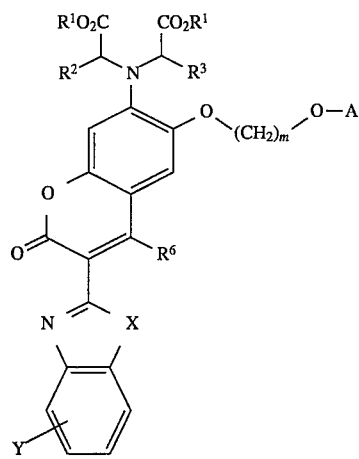

wherein m is either 2 or 3;

A is either of the formula

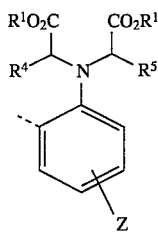

or A is of the formula

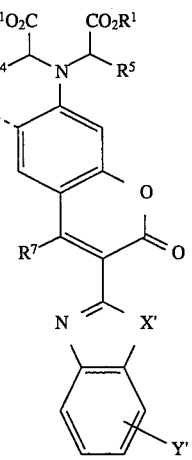

wherein $R^1$ is H, an alkyl group having 1–5 carbons, a benzyl, an alpha-acyloxyalkyl or a pharmaceutically acceptable esterifying group, a t-butyldimethylsilyl ester, or a pharmaceutically acceptable salt;

$R^2$, $R^3$, $R^4$ and $R^5$ are independently H or methyl;

$R^6$ and $R^7$ are independently H, CN, $CH_3$, $CF_3$ or $CONH_2$;

X and X' are independently O, S, or $C(CH_3)_2$;

Y and Y' are independently H, an alkyl having 1–18 carbons, $-NO_2$, $-NH_2$, $-NH(C=O)(CH_2)_n CH_3$, $-CF_3$, F, Cl, Br, I, $-OR^8$, $-CO_2R^9$, or $-OCH_2CO_2R^9$, where n=0–16; $R^9$ is H, an alkyl group having 1–18 carbons, a benzyl ($C_6H_5CH_2-$), an alpha-acyloxyalkyl, acetate, or a t-butyldimethylsilyl ether;

and $R^9$ is H, an alkyl group having 1–17 carbons, a benzyl ($C_6H_5CH_2$—) an alpha-acyloxyalkyl or other pharmaceutically acceptable esterifying group, a t-butyldimethylsilyl ester, or a pharmaceutically acceptable salt; or one of Y and Y' is a covalently attached conjugant; and Z is one of H, an alkyl having 1–18 carbons, —$NH_2$, —$NH(C=O)(CH_2)_nCH_3$, —$CF_3$, F, Cl, Br, I, —$OR^8$, —$CO_2R^9$, or —$OCH_2CO_2R^9$; or Z is a covalently attached conjugant;

b) illuminating said sample to generate an absorbance or fluorescence response; and c) observing said absorbance or fluorescence response.

17. A method, as claimed in claim 16, wherein the step of observing further comprises quantifying said absorbance or fluorescence response.

18. A method, as claimed in claim 17, wherein the step of observing is performed using a fluorometer, fluorescence microscope, laser scanner, or flow cytometer.

19. A method, as claimed in claim 16, wherein said polycationic metal ion is $Ca^{2+}$, $Mg^{2+}$ or $Zn^{2+}$.

20. A method, as claimed in claim 16, wherein said compound is present as part of a fiber optic probe.

21. A method, as claimed in claim 16, wherein said sample further comprises living cells or biological fluids.

* * * * *